United States Patent [19]
Robinson et al.

[11] Patent Number: 5,476,099
[45] Date of Patent: Dec. 19, 1995

[54] HIGH VELOCITY TISSUE SAMPLE CUTTER

[75] Inventors: Donald E. Robinson, Hopkinton, Mass.; Joseph E. Young, Loveland; Michael S. Banik, Cincinnati, both of Ohio

[73] Assignee: Boston Scientific Corporation, Watertown, Mass.

[21] Appl. No.: 299,196

[22] Filed: Aug. 31, 1994

[51] Int. Cl.⁶ .................................................. A61B 10/00
[52] U.S. Cl. ........................................................ 128/751
[58] Field of Search .......................... 128/749, 751–755; 606/167, 170

[56] References Cited

U.S. PATENT DOCUMENTS

| | | |
|---|---|---|
| 2,113,246 | 4/1938 | Wappler . |
| 3,608,544 | 9/1971 | Schnepper . |
| 3,675,688 | 7/1972 | Bryan et al. . |
| 3,692,020 | 9/1972 | Schied . |
| 3,840,003 | 10/1974 | Komiya . |
| 3,895,636 | 7/1975 | Schmidt . |
| 3,955,581 | 5/1976 | Spasiano et al. . |
| 3,989,033 | 11/1976 | Halpern et al. . |
| 4,427,014 | 1/1984 | Bel et al. . |
| 4,600,014 | 7/1986 | Beraha . |
| 4,620,547 | 11/1986 | Boebel . |
| 4,662,371 | 5/1987 | Whipple et al. . |
| 4,699,154 | 10/1987 | Lindgren . |
| 4,766,907 | 8/1988 | de Groot et al. . |
| 4,776,346 | 10/1988 | Beraha et al. . |
| 4,815,476 | 3/1989 | Clossick . |
| 4,830,002 | 5/1989 | Semm . |
| 4,880,015 | 11/1989 | Nierman .................. 128/751 |
| 4,881,551 | 11/1989 | Taylor . |
| 4,893,635 | 1/1990 | de Grott et al. . |
| 4,917,100 | 4/1990 | Nottke . |
| 4,924,878 | 5/1990 | Nottke . |
| 4,944,308 | 7/1990 | Akerfeldt . |
| 4,945,920 | 8/1990 | Clossick . |
| 4,953,558 | 9/1990 | Akerfeldt ................ 128/751 |
| 4,958,625 | 9/1990 | Bates et al. ............. 128/751 |
| 5,025,797 | 6/1991 | Baran . |
| 5,036,860 | 8/1991 | Leigh et al. . |
| 5,048,538 | 9/1991 | Terwilliger et al. . |
| 5,056,529 | 10/1991 | de Groot . |
| 5,074,311 | 12/1991 | Hasson . |
| 5,094,247 | 3/1992 | Hernandez et al. . |
| 5,100,430 | 3/1992 | Avellanet et al. . |
| 5,125,413 | 6/1992 | Baran . |
| 5,133,727 | 7/1992 | Bales et al. . |
| 5,147,380 | 9/1992 | Hernandez et al. . |
| 5,156,160 | 10/1992 | Bennett . |
| 5,170,800 | 12/1992 | Smith et al. . |
| 5,172,701 | 12/1992 | Leigh . |
| 5,174,300 | 12/1992 | Bales et al. . |
| 5,176,702 | 1/1993 | Bales et al. . |

(List continued on next page.)

FOREIGN PATENT DOCUMENTS

| | | |
|---|---|---|
| 0010321A1 | 4/1980 | European Pat. Off. . |
| 0318447A1 | 5/1989 | European Pat. Off. . |
| 141108 | 4/1980 | German Dem. Rep. . |
| 483829 | 1/1970 | Switzerland . |
| 175611 | 9/1964 | U.S.S.R. . |

*Primary Examiner*—Max Hindenburg
*Attorney, Agent, or Firm*—Fish & Richardson

[57] ABSTRACT

Samples of tissue are cleanly severed from locations deep within the body of a patient. A catheter has a catheter body constructed for placement through a narrow passageway and includes at its distal portion a cutter. The cutter includes a moveable cutting member that can be controllably actuated to sever the tissue sample from the location deep within the body. A firing mechanism is provided at a proximal end of the catheter. The firing mechanism includes, for example, a moveable actuating element connected to the cutting member and a preaccelerator element. The preaccelerator element is accelerated to high speed before transferring force to the actuating element to cause the actuating element to accelerate to rapidly actuate the moveable cutting member and cleanly cut the sample. The cutting element may be a jaw-form that has sharp end cutting edges and is constructed to provide shearing action.

28 Claims, 12 Drawing Sheets

U.S. PATENT DOCUMENTS

| | | |
|---|---|---|
| 5,195,533 | 3/1993 | Chin et al. . |
| 5,241,968 | 9/1993 | Slater . |
| 5,250,073 | 10/1993 | Cottone .................................. 128/751 |
| 5,318,589 | 6/1994 | Lichtman ................................ 128/751 |
| 5,383,471 | 1/1995 | Funnell .................................. 128/751 |
| 5,392,790 | 2/1995 | Kanner et al. ......................... 128/753 |
| 5,394,885 | 3/1995 | Francese ................................ 128/751 |

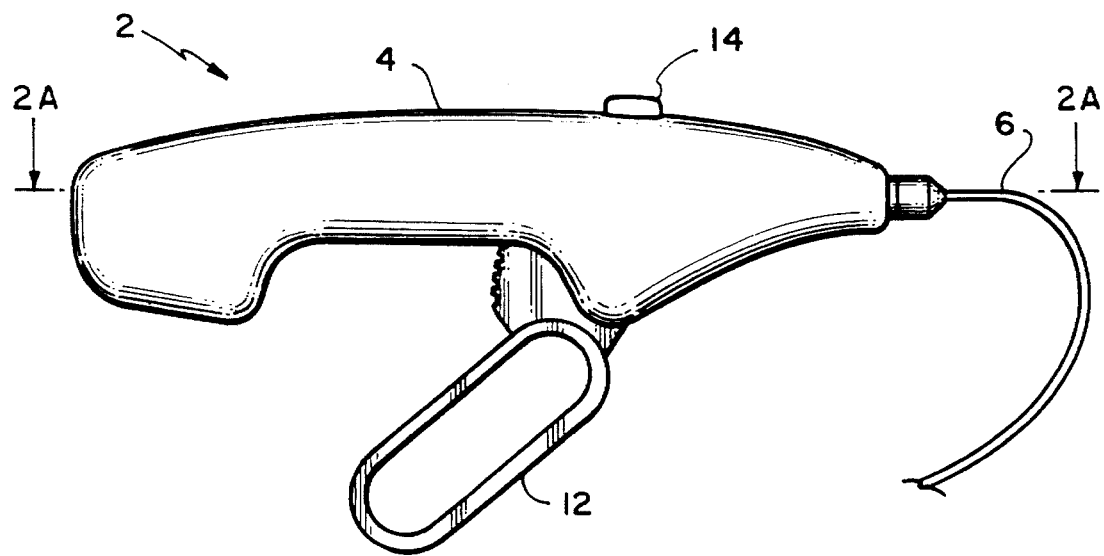
FIG. 1
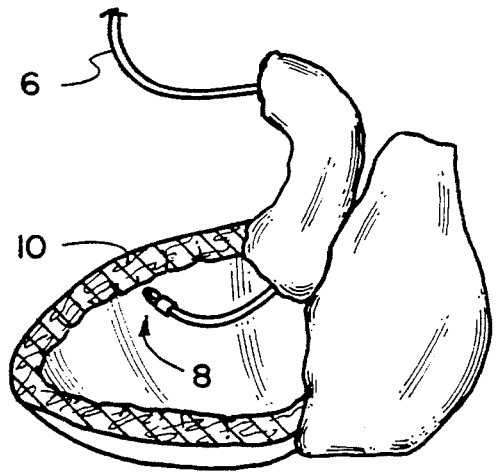

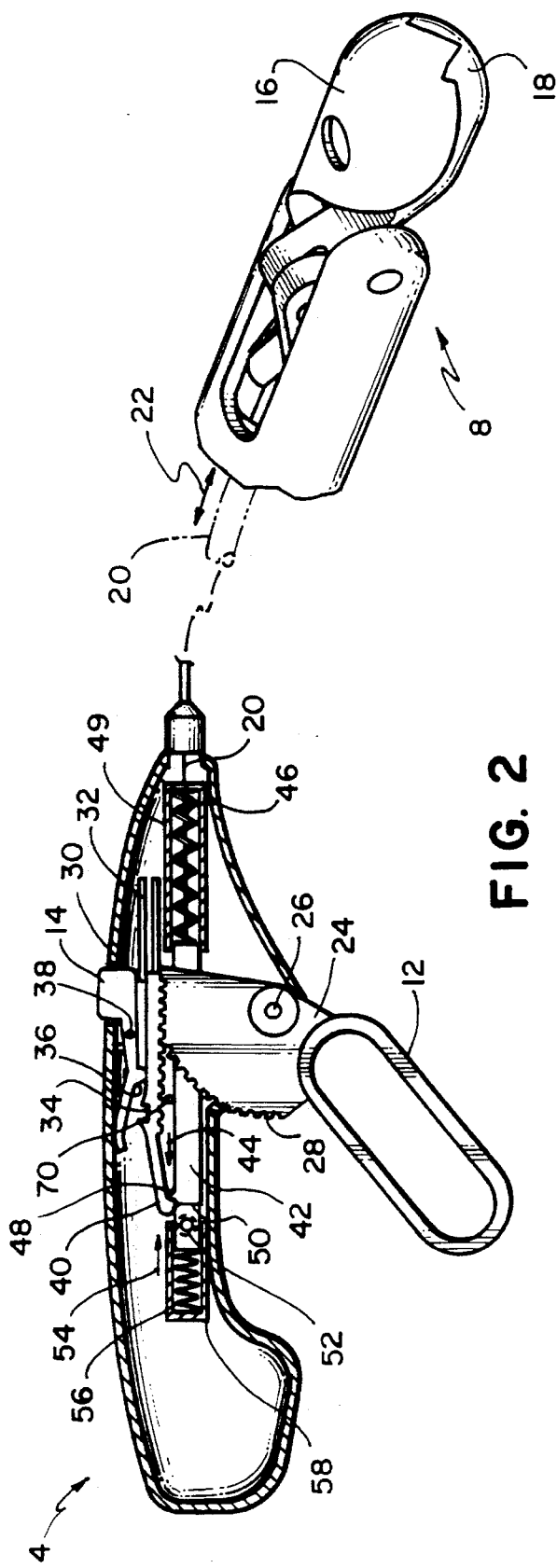
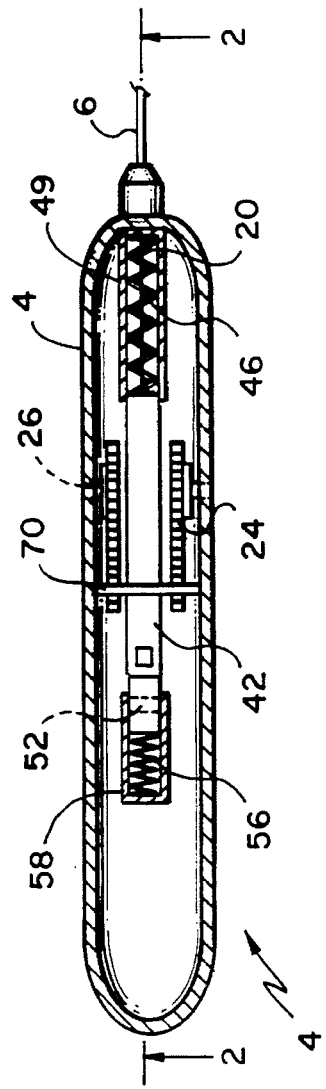

VELOCITY VS TRAVEL TIME

| TIME SEC | CYLINDER/JAW VELOCITY MM/S | RAM VELOCITY MM/S |
|---|---|---|
| 0 | 0 | 0 |
| 0.1 | 0 | 20 |
| 0.2 | 0 | 40 |
| 0.3 | 0 | 60 |
| 0.4 | 0 | 80 |
| 0.5 | 0 | 100 |
| 0.6 | 0 | 120 |
| 0.7 | 0 | 140 |
| 0.8 | 0 | 160 |
| 0.9 | 500 | 18 |
| 1.0 | 0 | 9 |
| 1.1 | 0 | 0 |

HIGH VELOCITY TISSUE SAMPLE CUTTER

FIELD OF THE INVENTION

This invention relates to taking samples of tissue from the body of a patient.

BACKGROUND OF THE INVENTION

Tissue samples can be examined in a laboratory to determine the presence of a pathological disorder. Often, the samples must be obtained from deep within the body using a medical sampling instrument that is introduced beneath the skin. For example, to diagnose heart transplant rejection, a catheter with a jaw-like cutter at its end is delivered through an artery or vein into the heart where it can bite a sample from the internal heart wall.

SUMMARY OF THE INVENTION

In a first aspect, the invention features a device for taking a sample of tissue from a location deep within the body of a patient. The device includes a catheter having a catheter body constructed for placement through a narrow passageway and including at its distal portion a cutter. The cutter has a moveable cutting member that can be controllably actuated to sever the tissue sample from the location deep within the body. The device also has a firing mechanism, including a moveable actuating element connected to the cutting member, and a ram element. The ram element can be accelerated and directed to transfer momentum to the actuating element to cause the actuating element to accelerate to rapidly to actuate the moveable cutting member and cleanly cut the sample.

In another aspect, the invention features a device for cleanly severing a sample of tissue from a location deep within the body of a patient. The device includes a catheter having a catheter body having an outer diameter of about 0.5 to 3.0 mm for placement through a narrow passageway and includes at its distal portion a cutter including a moveable jaw-form cutting member with sharp edges that can be controllably actuated to sever the tissue sample from the location deep within the body. The device also includes a firing mechanism including a moveable actuating element that can be accelerated to actuate the moveable cutting member to a maximum velocity of about 250 mm/sec or more over a distance of about 0.1 to 0.5 cm to cleanly cut the sample.

Embodiments may also include one or more of the following features. The ram element moves a greater distance before transferring the momentum than the actuating element moves to actuate the cutting member. The ram element has greater mass than the actuating element and cutting member. The moveable cutting member accelerates to a higher velocity than the maximum velocity of the ram. The actuating element moves about 0.2 to 1.0 cm to actuate the cutting element.

Embodiments may also include one or more of the following. The cutting member is accelerated to a velocity of 400–500 mm/sec. The ram element is spring biased. The ram element moves on a common axis with the actuating element. The ram is constructed to directly engage the actuating element to transfer the momentum. The actuator element is spring biased in a direction opposite the direction of bias of the ram element to cause the cutting member to move to an open position when the ram element is not engaging the actuating element. The firing mechanism is contained in a hand-held housing at a proximal end of the catheter and includes a lever for simultaneously energizing the ram element and moving the cutting element to an open position. The mechanism includes locking structure for placing the device in a sample removal condition with the cutting element in an open position and such that it will not rapidly actuate if the mechanism is accidentally fired. The ram element is partially loaded when the device is in the sample removal condition.

Embodiments may also include one or more of the following. The cutting element is a jaw-form constructed to sample from a tissue surface in front of the cutter. The cutter includes multiple moveable jaw-form cutting elements. The cutting element includes sharpened cutting edges. The cutter includes two jaw-form elements including a first jaw-form element being of greater size than a second jaw-form element such that a shearing force is applied to the tissue as the jaw-form elements approach each other for closure. The first, larger jaw-form element includes a flat surface that is engaged by the sharpened cutting surface of the second, smaller jaw-form element enclosure. The flat surface is an angular surface extending into the jaw. The jaws include complementary tooth structure. The jaws pivot about a common axis.

The inventions have many advantages. In particular, tissue samples can be cleanly severed from a tissue surface. The location from which the sample was taken heals with less scar tissue development because there is less tearing and trauma. The same location can be repeatedly sampled over time because, after healing, normal (non-scar) tissue is more likely to be present at the surface. These advantages are particularly important when sampling fibrous or muscular tissue, such as heart tissue in the area of the septum and the right ventricular apex, where repeated sampling may be necessary. Cleanly severing tissue also can improve the quality of the sample that is retrieved, making it more suitable for laboratory testing and therefore, minimizing the need to subject the patient to additional sampling operations because initial samples are unsuitable due to tearing and trauma which can destroy or modify the cells.

Tissue is cleanly severed by rapid motion of the cutting jaws. The motion of the jaws in the sampling system is rather small and therefore, their acceleration to high velocities must take place over very short times and distances. The jaws move substantially faster than manual jaw activation would permit. This jaw motion can be achieved with a firing mechanism that includes an actuating element that is held stationary until it is engaged by another, ram element, that has been accelerated to high speed, perhaps over a longer time and distance. The ram element instantly transfers momentum to the actuating element which causes it to rapidly accelerate in a short distance to snap the jaws shut.

The jaws have sharp cutting edges and are shaped to cause a shearing action upon tissue as they close. This can be achieved by jaws that are of slightly different axial lengths so the jaws are offset but still pivot about the same point. The sharp cutting edge of the smaller jaw meets a machined angular surface on the large jaw with a slight shearing action that cleanly severs tissue as the jaws close.

Further aspects, features, and advantages follow. For example, the invention also includes methods of manufacturing a sampling device and methods of sampling tissue. In one of the latter methods, a sampling device is provided that is capable of rapid jaw motion, the device is threaded through a tortuous lumen to a desired site, and the jaws are actuated to cleanly sever a sample. The device is removed from the body and the sample is retrieved. The method may also include allowing time to pass (e.g., several months) so that the site heals and then repeating the above steps to take an additional sample. The site may be in the heart. Multiple samples can be taken at different sites.

BRIEF DESCRIPTION OF THE DRAWINGS

FIG. 1 is a view of a device according to the invention illustrating the handle which remains outside the body and the distal end including a cutter positioned inside the heart where a sample is to be taken;

FIG. 2 is a view of the device in FIG. 1 with the handle portion in cross section and the cutter at the distal end in perspective, while FIG. 2a is a cross-sectional top view of the handle portion;

FIGS. 12–12b are further perspective views of the jaws.

DESCRIPTION OF THE PREFERRED EMBODIMENTS

Figure 3:
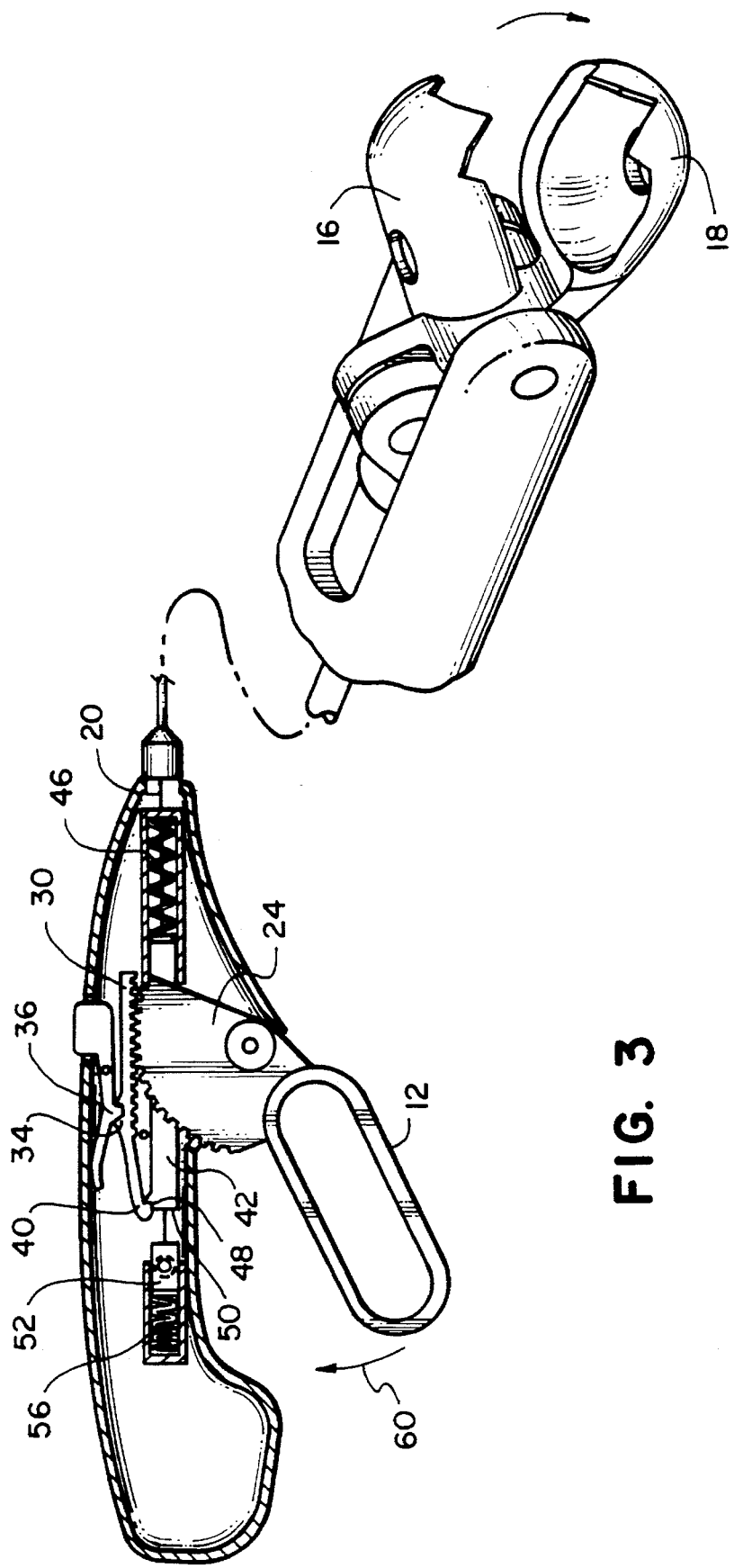
FIG. 3 is a view of the device in FIG. 2 with the firing mechanism positioned to open the jaws of the cutter.

Referring to FIG. 1, a device 2 for severing tissue includes a handle portion 4, a catheter portion 6, and a cutter portion 8. In the embodiment illustrated, the device 2 is constructed for sampling tissue from the interior of the heart 10. The catheter portion 6 is constructed so that it can be inserted through an introducer sheath and torqued and pushed from the proximal end through a long torturous passageway, such as the right internal jugular vein so that the physician can locate the cutter near the right ventricle apex. The catheter 6 is a torqueable, pushable laminate of PTFE and metal coils and has a length of about 50–100 cm (depending on jugular or, alternatively, femoral approach) and an outside diameter of about 1.8 to 2.2 mm. The catheter includes an internal lumen (not shown) through which a flexible control wire extends from a firing mechanism in the handle to the cutter. The proximal portion of the catheter, where it meets the handle portion 4, may include a strain relief.

Referring as well to FIGS. 2 and 2a, the cutter 8 has a pair of jaws 16, 18 which pivot into open and closed positions when control wire 20, which extends through the catheter 6 to the handle 4, is actuated axially (arrow 22). The handle portion 4, formed of two handle parts (e.g. plastic or metal) which are fastened together, is configured to be grasped in one hand by the physician. It includes an actuatable lever 12 through which the physician can place his last three fingers and a thumb button 14 for locking and unlocking the jaws of the cutter 8.

The handle 4 encloses the cutter firing mechanism which enables the jaws to be snapped shut at high speed to provide a smooth, clean cutting action. This advantage is achieved by accelerating a cylindrical ram 42 over a relatively long travel distance to very high velocities and then instantly transferring the momentum of the ram 42 to an actuating cylinder 52 such that it is rapidly accelerated over a short travel distance to snap the jaws shut at high speed.

The ram 42 is biased in the distal direction (arrow 44) by a stiff firing spring 46. The ram 42 is guided along its axial travel by guide surfaces 49 protruding from the inner walls of the housing 4. The ram 42 includes at its proximal portion a transverse protuberance 48 which is engaged by a hook 40 on a rack 30 during loading. The proximal end-surfaces 50 of the ram 42 face the distal end-surfaces 53 (FIG. 4) of an actuating cylinder 52. The actuating cylinder 52 is biased in the distal direction (arrow 54) by a compression spring 56, which is lighter than the firing spring 46. The actuating cylinder 52 is guided by guide surfaces 58 that protrude from the walls of the housing. The actuating cylinder is connected to the actuating wire 20 which extends through a lumen in the ram 42 (not shown), the firing spring 46, and the catheter to the cutter 8.

The firing mechanism also includes lever handle 12 which is rigidly attached to a pinion 24 that rotates about a pin 26 attached to the handle. The teeth 28 of the pinion 24 mesh with a rack 30 that is axially moveable and guided by guide shims 32 in the walls of the handle. The rack 30 also includes a locking surface 34 that can receive locking protuberance 36 on an extension of the locking button 14, which pivots about pin 38. The rack 30 further includes grasping hook 40 for loading the ram in preparation for firing. The system also includes a release post 70, protruding from the inner walls of the housing, to deflect the hook from the ram to fire the device as will be described in more detail below.

Referring as well to FIG. 3, to operate the device to take a sample, the lever 12 is rotated clockwise (arrow 60) which rotates the pinion 24 and slides the rack 30. The rack hook 40 engaging the protuberance 48 on the ram 42 moves the ram distally and begins to compress the firing spring 46. The proximal end-surface 50 of the ram is separated from the actuating cylinder 52 which also moves distally under the force of compression spring 56. With the distal movement of the actuating cylinder 52, the control wire 20 moves distally opening the jaws 16, 18. In this configuration, the trigger protuberance 36 is within the rack locking surface 34 and the jaws are locked in the open position.

The physician may also place the device in this condition after taking a sample to lock the jaws in the open position and remove the sample from within. An advantage of this arrangement is that, even if the jaws are unlocked by mistake, they will not snap shut at high velocity since the firing spring has only been partially compressed. In the case of accidental unlocking, the ram would move relatively slowly into engagement with the actuating cylinder and the compression spring 56 would oppose the motion of the actuating cylinder to prevent substantial rapid closure of the jaws. Thus, a sample can be retrieved from the jaws by the physician with reduced risk.

Figure 4:
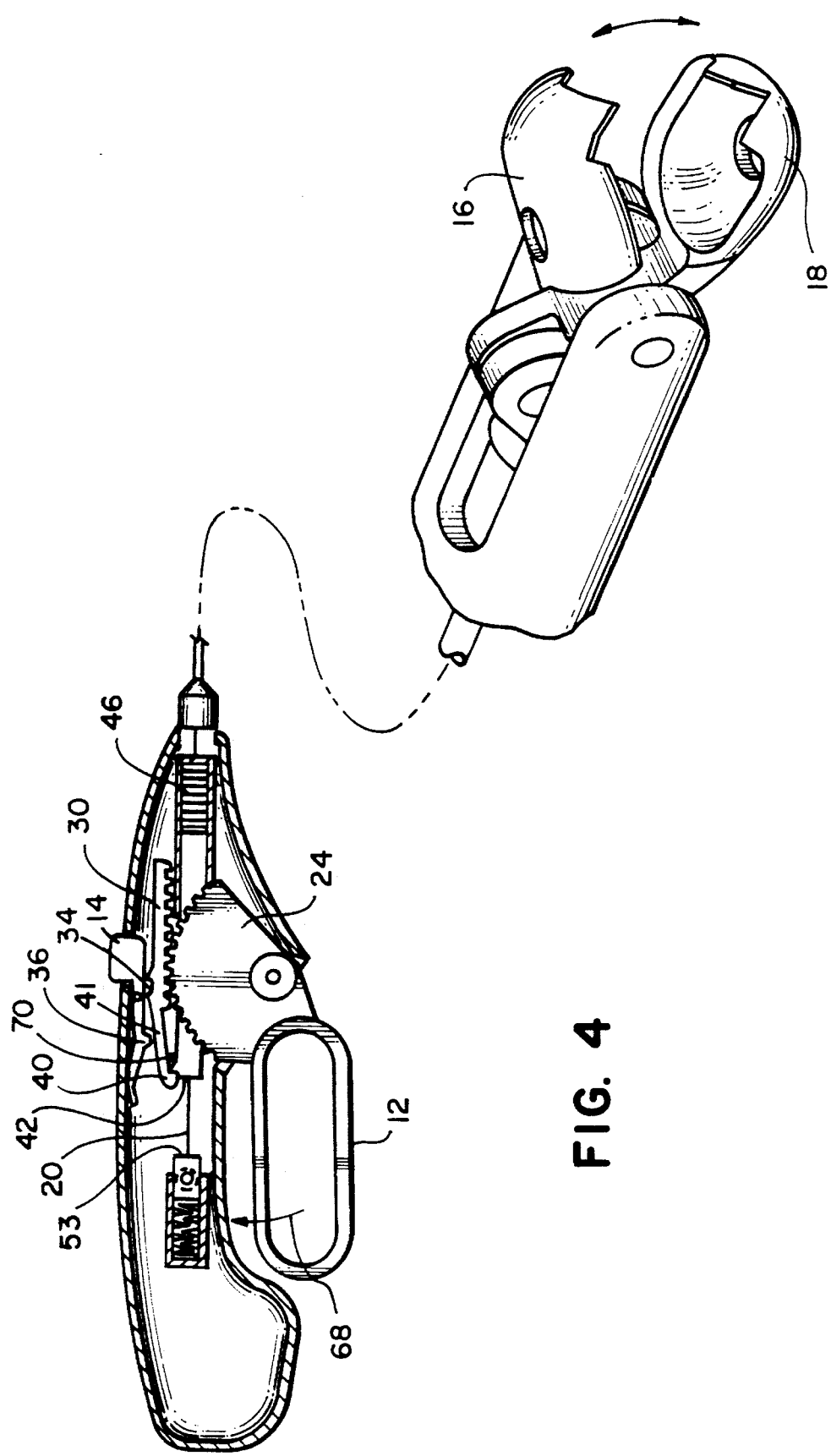
FIG. 4 is a view of the device in FIG. 3 with the firing mechanism in a state that is ready to close the jaws of the cutter to take a sample.

Referring as well to FIG. 4, to fire the jaws, the thumb button 14 is actuated to remove locking protuberance 36 from the locking surface 34 on the rack and lever 12 is further rotated clockwise (arrow 68) to fully compress the firing spring 46. When the rack reaches a position where the inner surface of the angular shank portion 41 of hook 40 engages a release post 70, the hook is deflected away from engagement with the protuberance 48 on the ram 42.

Figure 5:
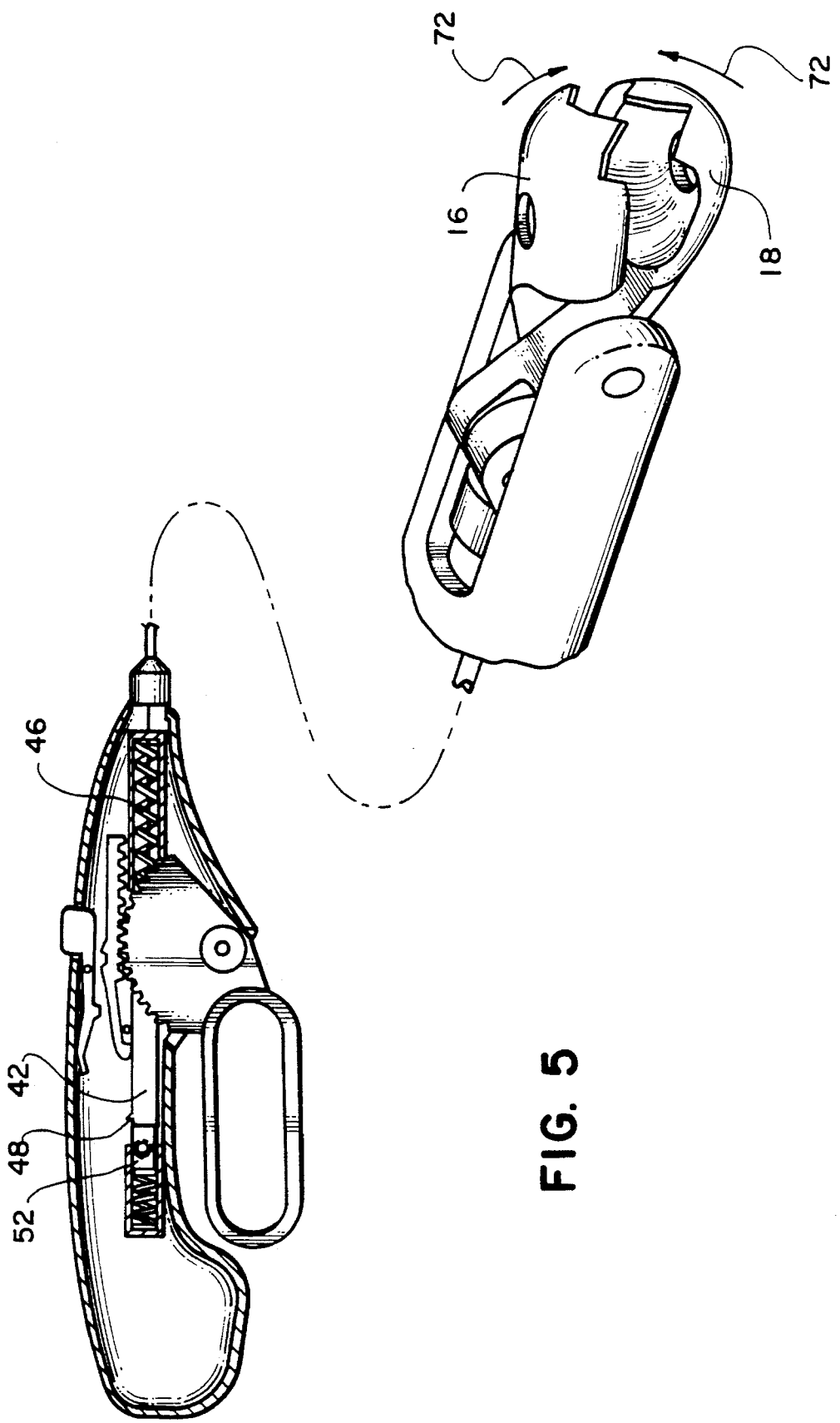
FIG. 5 is a view of the device in FIG. 4 with the jaws in the process of being snapped shut.
Figure 6:
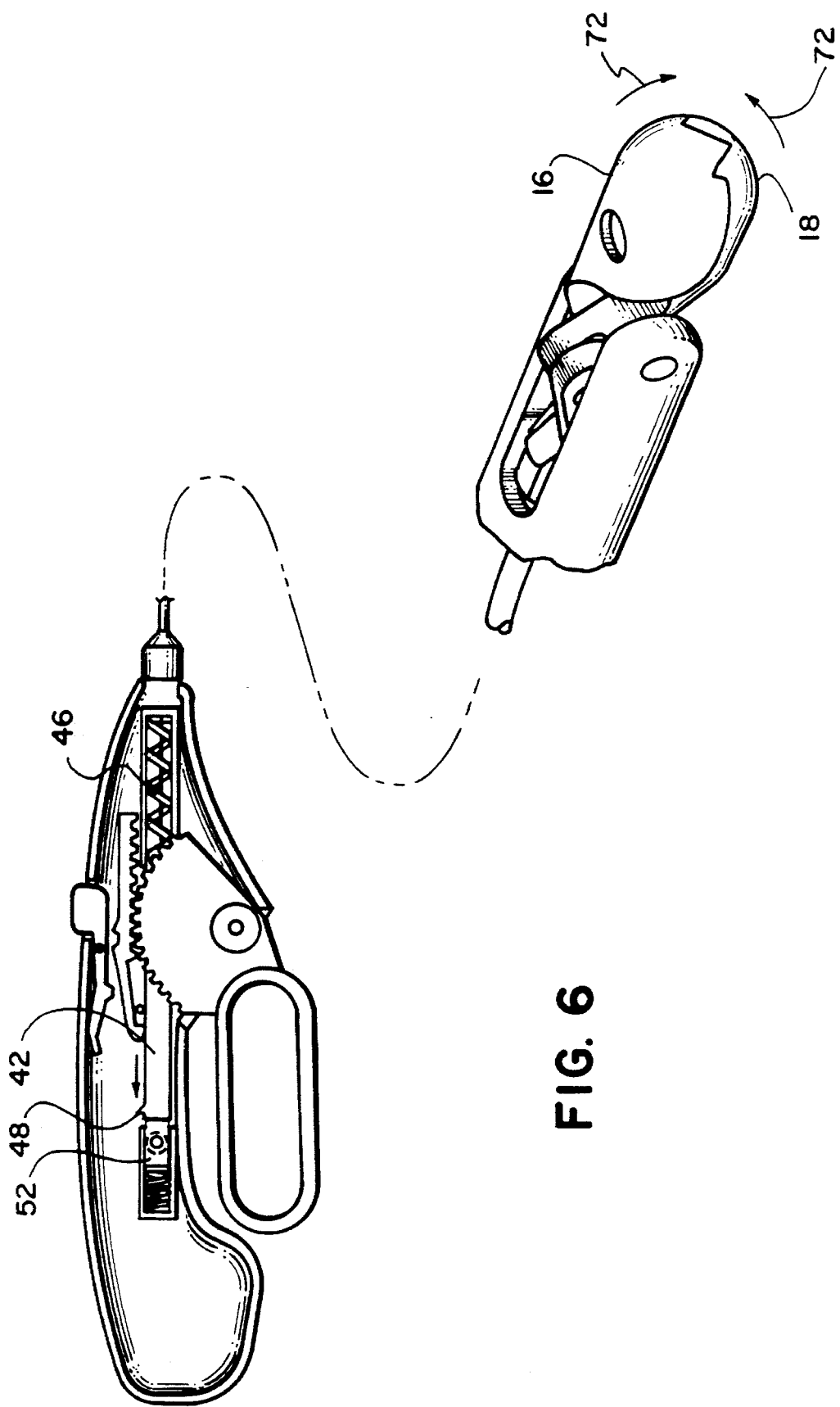
FIG. 6 is a view of the device in FIG. 5 with the jaw closure complete.

Referring as well to FIGS. 5 and 6, the ram 42 is then released and accelerated rapidly in the distal direction under the power of the firing spring 46. When the ram 42 reaches a high velocity, its distal end surface 50 engages the proximal end surface 53 of the actuating cylinder 52 with great force. The momentum transfer causes the actuating cylinder 52 to rapidly accelerate to high velocity in the distal direction, pulling the control wire 20, and rapidly snapping the jaws shut (arrows 72) for cleanly severing a tissue sample.

Figures 7, 7A:
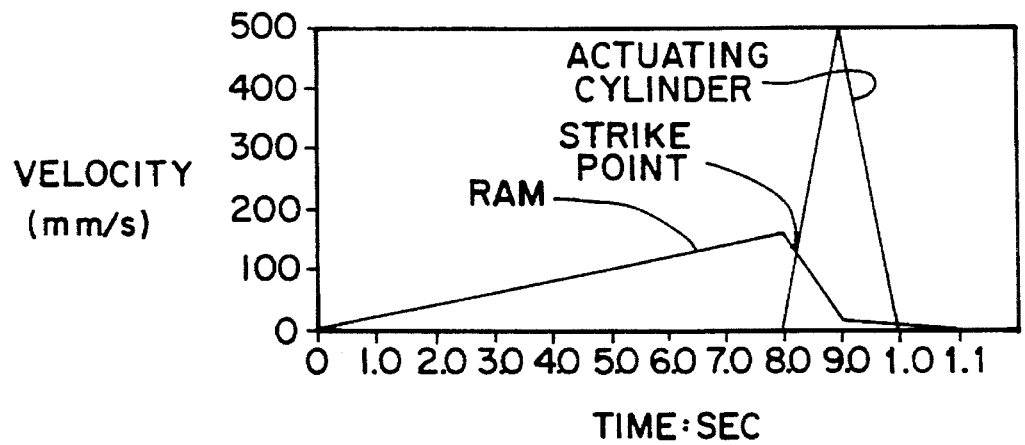
FIGS. 7 and 7a are a plot and tabulation, respectively, of velocity versus travel distance for a firing mechanism ram and for an actuating cylinder.

Referring to FIGS. 7 and 7a, velocity profiles of the ram and of the actuating cylinder (which substantially corresponds to the velocity of the jaws) are illustrated. As the graph shows, after the ram is released, the ram velocity increases over a substantial time and distance until near the strike point where the ram strikes the actuating cylinder. Thereafter, the ram velocity rapidly decreases, its momentum having been transferred to the actuating cylinder. The actuating cylinder velocity increases rapidly from the strike point over a short travel distance to jaw closure at which point its velocity and the jaw velocity drops to zero.

Figure 11:
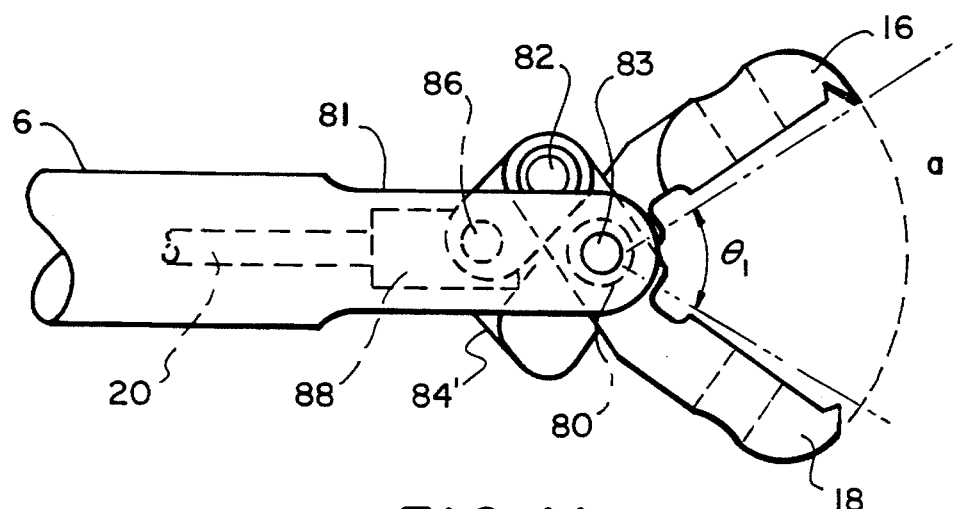
FIG. 11 is a side view of the distal end of the device, illustrating the coupling of the jaws to the device.
Figure 12:
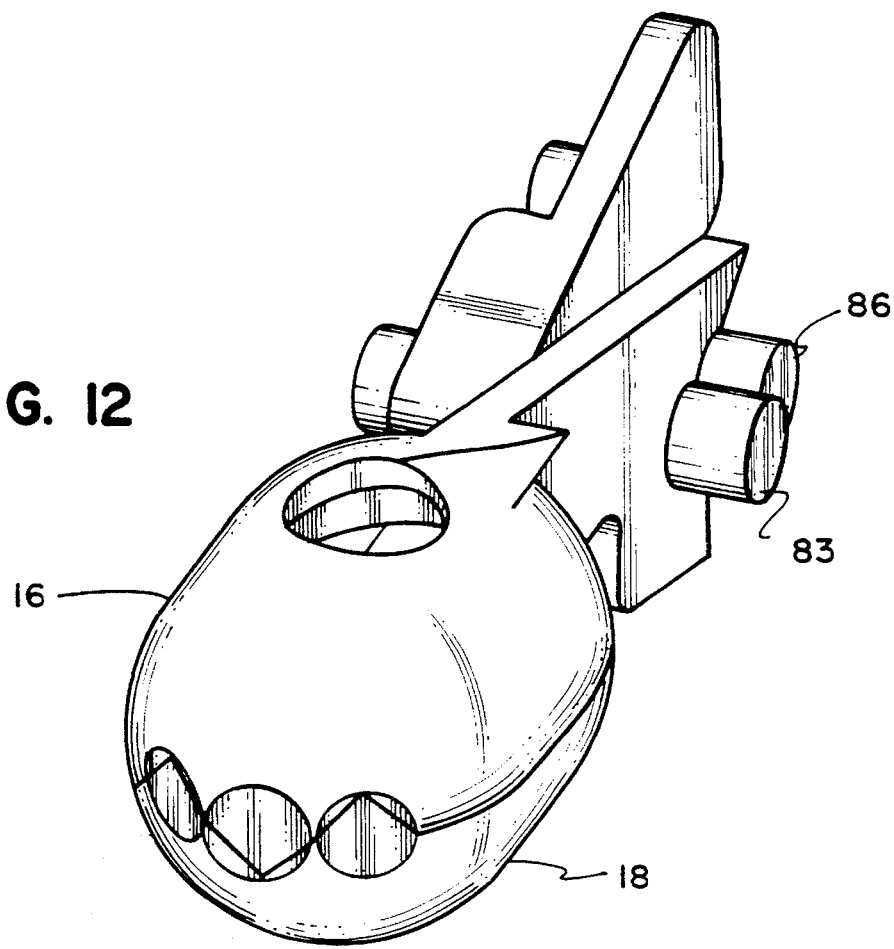
Figure 12:
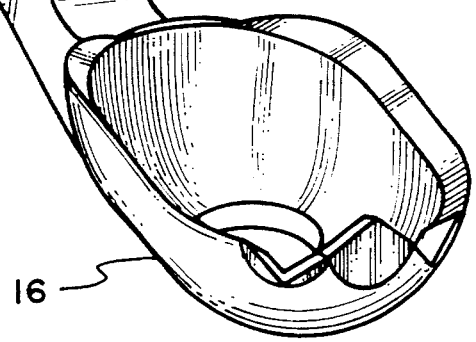
Figure 12:
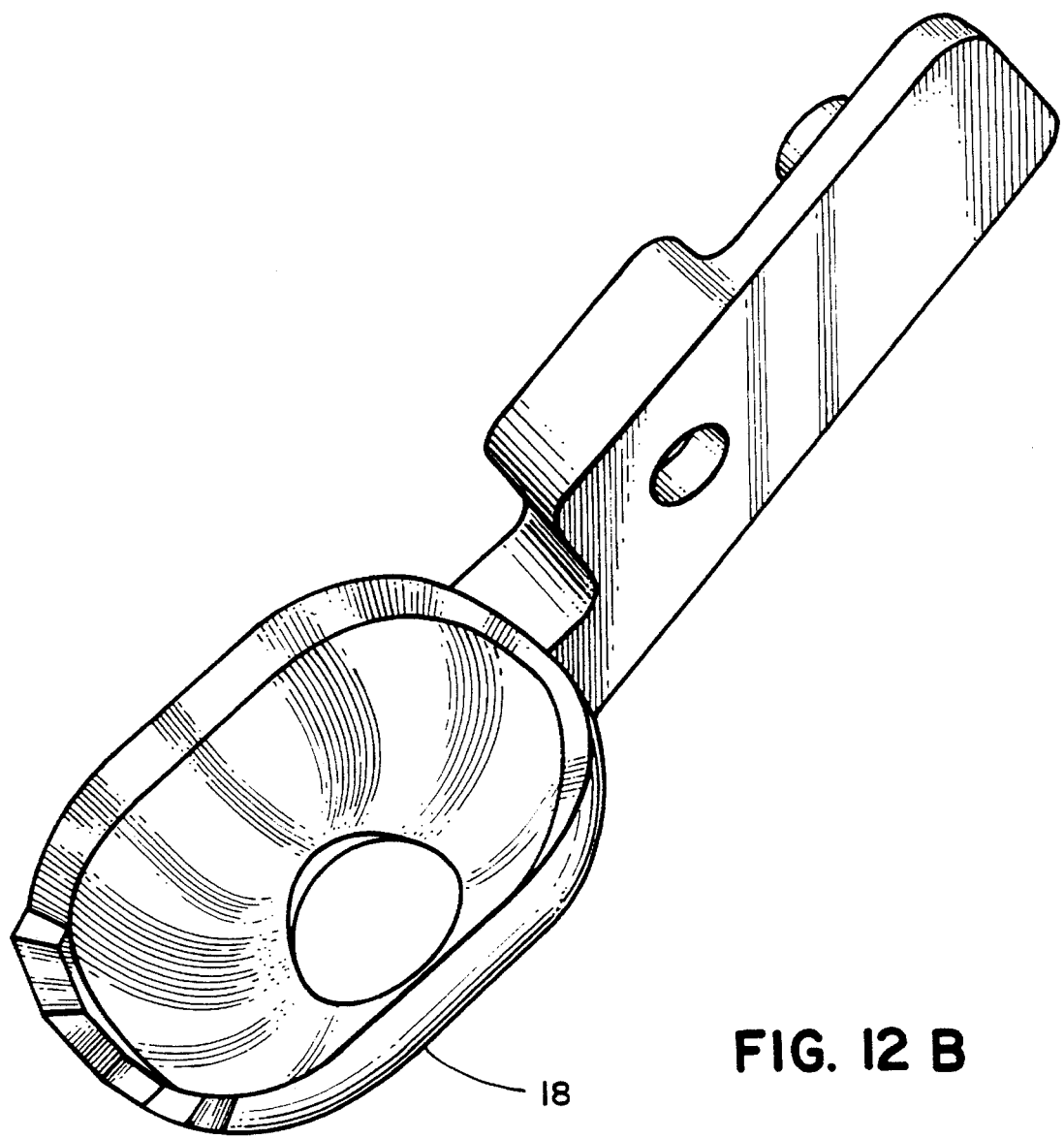

In a particular embodiment, the ram travel distance to the strike point is about 1.6 cm and in that distance it achieves a maximum velocity of about 100–200 mm/sec. The actuating cylinder has a travel distance of about 0.45 cm before jaw closure and achieves a maximum velocity of about 400–500 mm/sec. The ram is more massive than the actuating cylinder and preferably more massive than the combined mass of the actuating cylinder, control wire, and jaws. For example, the ram may be formed of steel with a weight of about 27 g and the actuating cylinder is formed of aluminum with a weight of about 2–2.5 g. The control wire is stainless steel with a diameter of about 0.020 mm and weighs about 1.2 g. Each jaw weighs about 0.03 g. The spring rate of the firing spring is 28 lbs./inch. The spring rate of compression spring 56 is about 1.75 lbs/inch. The jaws open to a maximum arc angle of, $\theta_1$, about 95°–100° (FIG. 11). The maximum arc distance, a, of jaw travel is about 0.3 cm for each jaw (FIG. 11). The jaws in the closed position have an outer diameter of about 1.7 to 2.2 mm.

Figure 8:
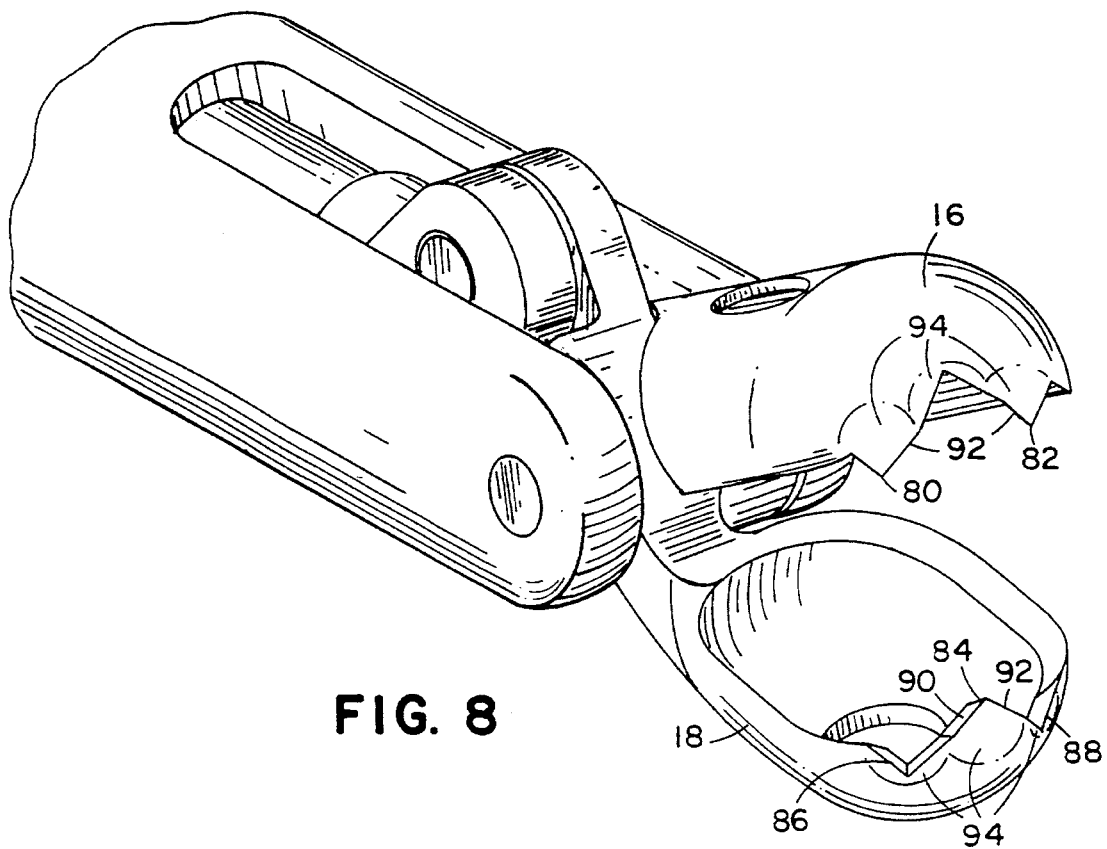
FIG. 8 is a greatly enlarged view of the jaws.

Referring to FIG. 8, the clean severing of tissue is also enhanced by jaws with teeth and sharp cutting surfaces and, in particular, jaws that provide a degree of shearing action upon closure. The jaw 16 includes two extending teeth 80, 82 with a region therebetween for mating with a single tooth 84 on jaw 18. Jaw 18 includes regions 86, 88 to receive the teeth 80, 82. The nonidentical jaws provide a three-point arrangement at the front of the jaws that stabilizes the device as tissue is pierced during closure. This feature is particularly beneficial when taking samples from pulsating tissue surfaces, such as in the heart and can avoid the need for a stabilizing prong within the jaws.

The teeth and inner surfaces of the jaws are machined to include inward angled surfaces 90, sharp outer edges 92, and flat outer surfaces 94. One jaw, jaw 16, is slightly shorter and narrower than the other jaw, jaw 18, so that upon closure, the sharp cutting surface 92 of jaw 16 meets the inwardly angled surfaces 90 on jaw 18 in a slight shearing action. The design permits samples to be taken from directly in front of the jaws. The flat angular inner contour is machined to sharpen the outer edges of the jaws. The length and width mismatch between the jaws is typically in the range of about 0.001 to 0.004 inch.

Figure 9:
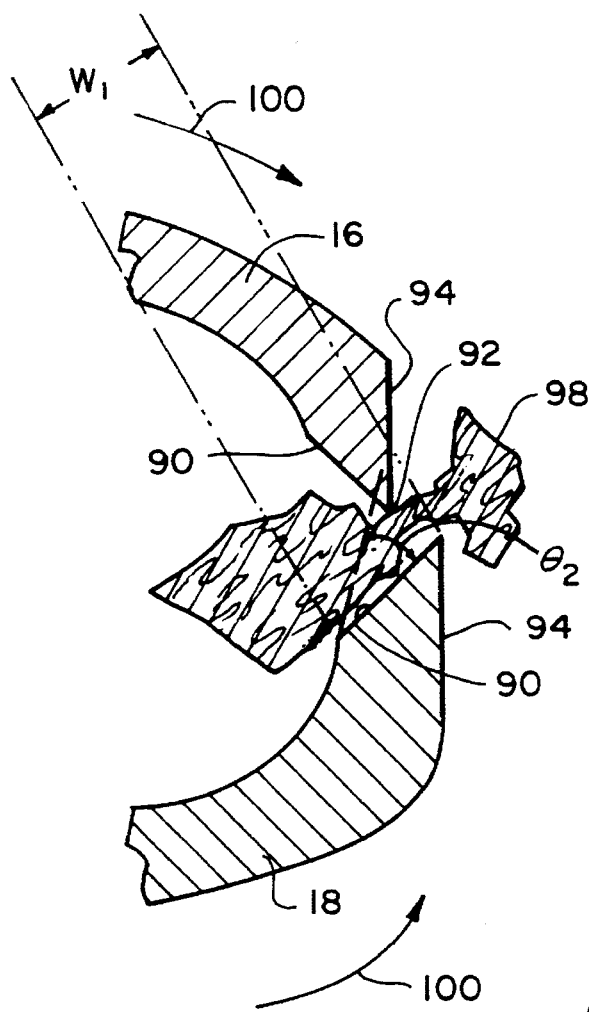
FIGS. 9 and 9a are cross-sectional side views illustrating the shearing action of the jaws.
Figure 9A:
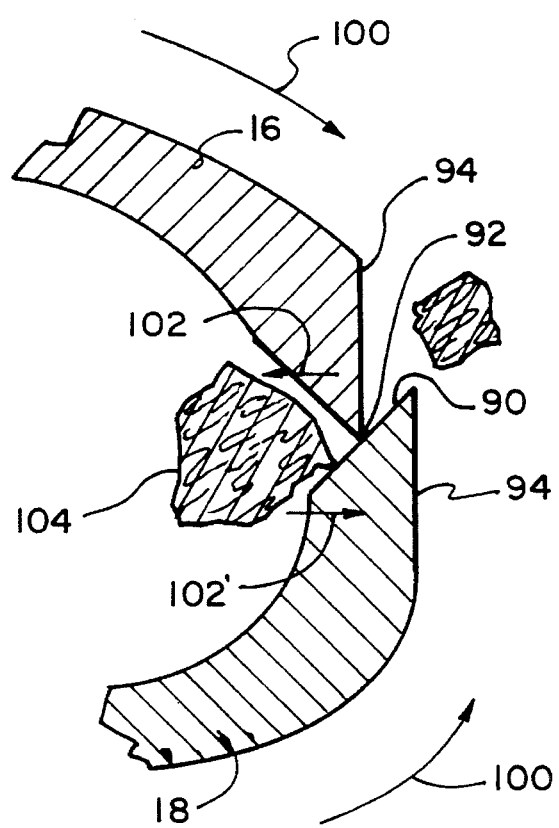

Referring to FIGS. 9 and 9a, which are cross-sectional views through a portion of the jaws as they come together upon closure to sever tissue 98, as the jaws rotate toward each other (arrows 100), tissue becomes positioned between the sharpened surface 92 of jaw 16 and the flat angled surface 90 of jaw 18 (FIG. 9). As the jaw closure is completed, the sample is sheared off by a slight relative shearing motion along the device axis (arrows 102, 102') as the sharp edge 92 of jaw 16 engages the surface 90 of jaw 18 to sever a sample 104 (FIG. 9a).

Figure 10:
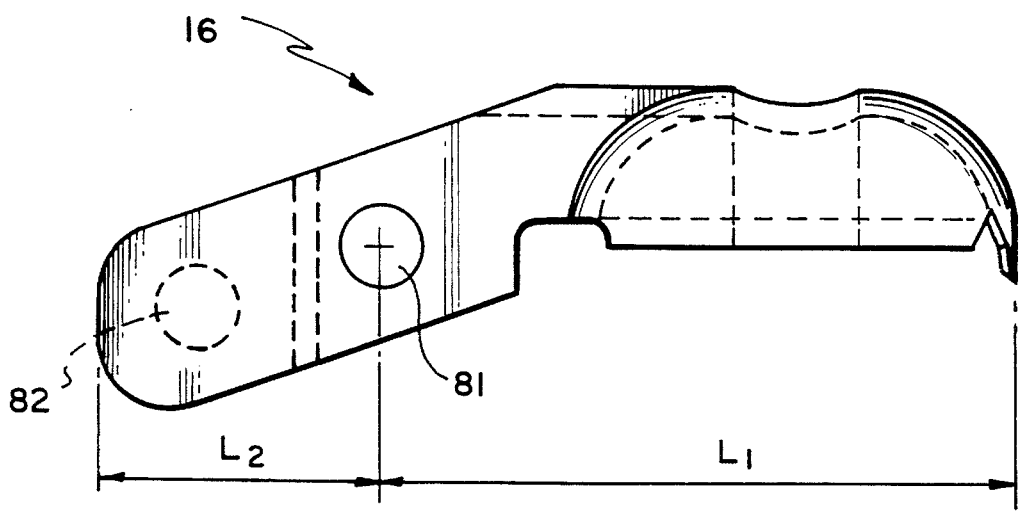
FIGS. 10 and 10a are side views of the jaws.
Figure 10A:
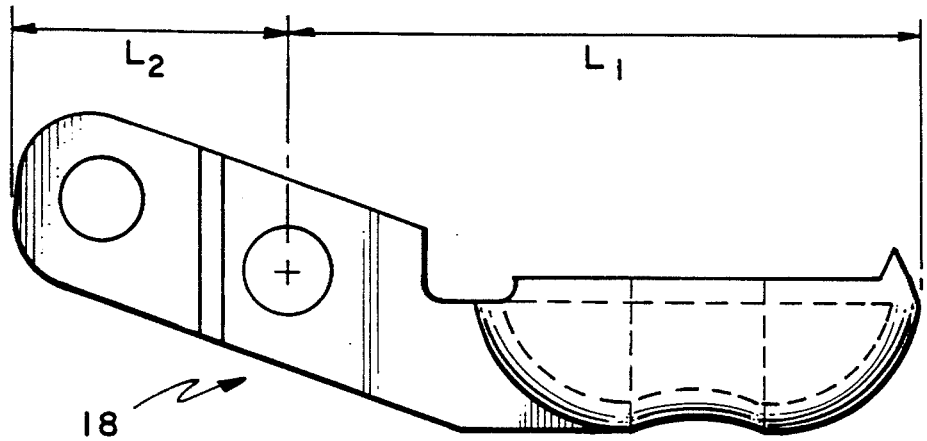

Referring to FIGS. 10 and 10a, in an embodiment, the jaws are formed of stainless steel by five-axis machining (Wilhemin Machine, Switzerland). The smaller jaw, jaw 16, extends a length $L_1$, from a pivot opening 80, of about 0.137 inch and has a width of about 0.069 inch. The large jaw, jaw 18, extends a length, $L_1'$, about 0.138 inch, and has a width of about 0.070 inch. The surfaces 90 are angled at, $\theta_2$, about 40° and extend for a width, $W_1$, of about 0.008 inch (FIG. 9). The jaws extend a distance $L_2$, about 0.060 inch along an angled actuating portion which includes a post 82.

Referring particularly to FIG. 11, the jaws are coupled to the catheter 6 at a clevis portion 81, which includes pins 83 that pass through the pivot openings 80. The posts 82 on the actuating portion of the jaws fit through distal openings in links 84, 84'. The links 84, 84' includes proximal openings through which posts 86 (opposite post not shown) extend. The posts are attached to a yoke 88, which is in turn attached to control wire 20. A coupling mechanism of this type is available in a commercial heart tissue sampling system, the Mansfield Bycep Endomvocardial Biopsy Forceps, available from Boston Scientific Corp., Watertown, Mass.

Still further embodiments are within the claims. For example, the device may include a deflectable, steerable end by using a tension wire that can be pulled from the proximal end and locked in a desired orientation. The inventions can be used to advantage in many areas besides the heart or vascular system. For example, the devices can be constructed for use in the gastrointestinal or urinary tract. Rapid jaw motion for clean cutting may be provided by other mechanisms, such as a pneumatics, solenoid, or electromechanical switches. The pivot opening of one of the jaws can be slotted to provide a scissoring action. The jaws can be manufactured by injection molding (e.g. of plastic), or by stamping, with, for example, post-forming machining to sharpen the edges or by metal injection molding.

What is claimed is:

1. A device for taking a sample of tissue from a location deep within the body of a patient, comprising:

a catheter having a catheter body constructed for placement through a narrow passageway and including at its distal portion a cutter including a moveable cutting member that can be controllably actuated to sever said tissue sample from said location deep within the body, and a firing mechanism including a moveable actuating element connected to said cutting member, and a ram element that can be accelerated and directed to transfer momentum to said actuating element to cause said actuating element to accelerate to rapidly actuate said moveable cutting member and cleanly cut said sample.

2. The device of claim 1 wherein said ram element moves a greater distance before transferring said momentum than said actuating element moves to actuate said cutting member.

3. The device of claim 1 or 2 wherein said ram element has greater mass than said actuating element and cutting member.

4. The device of claim 1 or 2 wherein said moveable cutting member accelerates to a higher velocity than the maximum velocity of said ram.

5. The device of claim 1 wherein said actuating element moves about 0.2 to 1.0 cm to actuate said cutting element.

6. The device of claim 1 wherein said cutting element is actuated at a maximum velocity of about 250 mm/sec or more over a distance of 0.1 to 0.5 cm.

7. The device of claim 1 wherein said ram element is spring biased.

8. The device of claim 7 wherein said ram element moves on a common axis with said actuating element.

9. The device of claim 8 wherein said ram is constructed to directly engage said actuating element to transfer said momentum.

10. The device of claim 9 wherein said actuator element is spring biased in a direction opposite the direction of bias of said ram element to cause said cutting member to move to an open position when said ram element is not engaging said actuating element.

11. The device of claim 1 wherein said firing mechanism is contained in a hand-held housing at a proximal end of said catheter and includes a lever for simultaneously energizing said ram element and moving said cutting element to an open position.

12. The device of claim 11 wherein said mechanism includes locking structure for placing said device in a sample removal condition with said cutting element in an open position and such that it will not rapidly actuate if said mechanism is accidentally fired.

13. The device of claim 12 wherein said ram element is partially loaded when said device is in said sample removal condition.

14. The device of claim 1 wherein said cutting element is a jaw-form constructed to sample from a tissue surface in front of said cutter.

15. The device of claim 14 wherein said cutter includes multiple moveable jaw-form cutting elements.

16. The device of claim 1 wherein said cutting element includes sharpened cutting edges.

17. The device of claim 16 wherein said cutter includes two jaw-form elements including a first jaw-form element being of greater size than a second jaw-form element such that a shearing force is applied to said tissue as said jaw-form elements approach each other for closure.

18. The device of claim 17 wherein said first, larger jaw-form element includes a flat surface that is engaged by the sharpened cutting surface of said second, smaller jaw-form element upon enclosure.

19. The device of claim 18 wherein said flat surface is an angular surface extending into said jaw.

20. The device of claim 19 wherein said jaws include complementary tooth structure.

21. The device of claim 17 wherein said jaws pivot about a common axis.

22. A device for cleanly severing a sample of tissue from a location deep within the body of a patient, comprising:

a catheter having a catheter body having an outer diameter of about 0.5 to 3.5 mm for placement through a narrow passageway and including at its distal portion a cutter including a moveable jaw-form cutting member with sharp edges that can be controllably actuated to sever said tissue sample from said location deep within the body, and a firing mechanism including a moveable actuating element that can be accelerated to actuate said moveable cutting member to a maximum velocity of about 250 mm/sec or more over a distance of about 0.1 to 0.5 cm to cleanly cut said sample.

23. The device of claim 22 wherein said moveable cutting member is accelerated to a maximum velocity of 400–500 mm/sec.

24. The device of claim 22 or 23 wherein said device includes a pair of moveable jaw-form cutting members.

25. The device of claim 24 wherein said cutter includes two jaw-form elements including a first jaw-form element being of greater size than a second jaw-form element such that a shearing force is applied to said tissue as said jaw-form elements approach each other for closure.

26. The device of claim 3 wherein said cutting element is a jaw-form constructed to sample from a tissue surface in front of said cutter.

27. The device of claim 4 wherein said cutting element is a jaw-form constructed to sample from a tissue surface in front of said cutter.

28. The device of claim 7, 8, 9, or 11 wherein said cutting element is a jaw-form constructed to sample from a tissue surface in front of said cutter.

* * * * *